US005935812A

United States Patent [19]
Bandman et al.

[11] Patent Number: 5,935,812
[45] Date of Patent: *Aug. 10, 1999

[54] HUMAN GTP BINDING PROTEIN GAMMA-3

[75] Inventors: Olga Bandman, Mountain View; Surya K. Goli, Sunnyvale; Lynn E. Murry, Portola Valley, all of Calif.

[73] Assignee: Incyte Pharmaceuticals, Inc., Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/715,527

[22] Filed: Sep. 18, 1996

[51] Int. Cl.$^6$ ........................................ C12P 21/00
[52] U.S. Cl. .................. 435/69.1; 435/252.3; 435/320.1; 536/23.1; 530/300; 530/350
[58] Field of Search ........................ 536/23.1; 435/320.1, 435/240.2, 69.1, 252.3; 530/300, 350

[56] References Cited

FOREIGN PATENT DOCUMENTS

WO9637513  11/1996  WIPO .

OTHER PUBLICATIONS

Morishita et al. (1994) FEBS Letters 337, pp. 23–26, 1994.
Morishita et al. (1994) GenBank, Accession No. A36204, 1994.
Kalyanaraman, S., et al., "A Brain–Specific G Protein Gamma Subunit," *Biochemical and Biophysical Research Communications,* 216(1)1995 pp. 126–132.
Hillier, L. et al. (1995) EST–STS database submissions, accession nos.: R88618, R87582, H44165, H22621, H40975, H44910, H44159, H23781, H18201, R84606, 1995.
Intelligenetics Suite Release 5.4 (Jan. 1993) Advanced Training Manual, Intelligenetics, Inc. 700 E. El Camino Real, Mountain View, CA 94040, 1993.
Aussel, C. et al., "Inhibition and Activation of Interleukin 2 Synthesis by Direct Modification of Guanosine Triphosphate–Binding Proteins", *J Immunol,* 1988, vol. 140, pp. 215–220.

Clapman, D. et al., "New Roles for G–Protein βγ–Dimers in Transmembrane Signalling", *Nature,* 1993, vol. 365, pp. 403–406.
Gautam, N. et al., "G Protein Diversity is Increased by Associations with a Variety of γ Subunits", *Proc Natl Acad Sci,* 1990, vol. 87, pp. 7973–7977. (Accession 163084).
Iyengar, R. et al., "Molecular and Functional Diversity of Mammalian $G_S$–Stimulated Adenylyl Cyclases", *FASEB Jour,* 1993, vol. 7, pp. 768–775.
Neer, E. et al., "Heterotrimeric G Proteins: Organizers of Transmembrane Signals", *Cell,* 1995, vol. 80, pp. 249–257.
Ray, K. et al., "Isolation of cDNA Clones Encoding Eight Different Human G Protein γ Subunits, Including Three Novel Forms Designated the $γ_4$, $γ_{10}$, and $γ_{11}$ Subunits", *Biol Chem,* 1995, vol. 270, pp. 21765–21771 (Accession 995917).
Stephens, L. et al., "A Novel Phosphoinositide 3 Kinase Activity in Myeloid–Derived Cells is Activated by G Protein βγ Subunits", *Cell,* 1994, vol. 77, pp. 83–93.
Williams, CJ et al., "G Protein Gene Expression During Mouse Oocyte Growth and Maturation, and Preimplantation Embryo Development", *Mol Reprod Dev,* 1996, vol. 44, pp. 315–323. (Accession 1353498).

*Primary Examiner*—Robert A. Wax
*Assistant Examiner*—Enrique Longton
*Attorney, Agent, or Firm*—Lucy J. Billings, Esq.; Leanne C. Price, Esq.; Incyte Pharmaceuticals, Inc.

[57] ABSTRACT

The present invention provides a polynucleotide which identifies and encodes a novel human GTP binding protein gamma-3 (HGPG) and HGPG itself. The invention provides for genetically engineered expression vectors, host cells containing the vector and a method for producing HGPG. The invention also provides a method for identifying pharmaceutical compositions inhibiting the expression and activity of HGPG and for the use of such compositions for the treatment of cancer. The invention also provides diagnostic assays which utilize the polynucleotide to hybridize with the transcripts encoding HGPG or anti-HGPG antibodies which specifically bind to HGPG in normal or diseased tissues.

5 Claims, 5 Drawing Sheets

```
                      9                18               27              36              45              54
5' NCC TTC AGG TAC CAG CCA AGA CAG TGC TTG AGC TGC AGA AAC TGA GAC CAG 63                72               81              90              99             108
   ACC TCT GGC CTG GCC CTC CCC AGG GGC CTC CTT TCC TAT AGT CAC TGC TTC TGC 117               126              135             144             153             162
   ATC AGA TAC TTT CAG CTG CAA CTC CCT ACT GGG GGC TGG ACC CAT TTC AGG CAG 171               180              189             198             207             216
   AAG GTT TTG GTA CCC TCC ACT GAC CCT ACA CCC AGG GCT GCT ACT GCC GCT TGT 225               234              243             252             261             270
   GGC TTC AGG ATG AAA GGT GAG ACC CCG GTG AAC AGC ACT ATG AGT ATT GGG CAA
                        M   K   G   E   T   P   V   N   S   T   M   S   I   G   Q 279               288              297             306             315             324
   GCA CGC AAG ATG GTG GAA CAG CTT AAG ATT GAA GCC AGC TTG TGT CGG ATA AAG
    A   R   K   M   V   E   Q   L   K   I   E   A   S   L   C   R   I   K 333               342              351             360             369             378
   GTG TCC AAG GCA GCA GAC CTG ATG ACT TAC TGT GAT GCC CAC GCC TGT GAG
    V   S   K   A   A   D   L   M   T   Y   C   D   A   H   A   C   E
```

FIGURE 1A

```
      387         396         405         414         423         432
GAT CCC CTC ATC ACC CCT GTG CCC ACT TCG GAG AAC CCC TTC CGG GAG AAG AAG
 D   P   L   I   T   P   V   P   T   S   E   N   P   F   R   E   K   K 441         450         459         468         477         486
TTC TTC TGT GCT CTY CTC TGA GCT CCC CTG TCC CTT CTC ACA ACT SCT CCC TTT
 F   F   C   A   L   L 495         504         513         522
TCC CTC TCC TGG GCC CTT CCT TAG GTC AGT AAT TGT TGT GAG  3'
```

```
 1  MKGETPVNSTMSIG-----QARKMVEQLKIEASLCRIKVSKAAAD   112808
 1  ------MKEGMSNNSTTSISQARKAVEQLKMEACMDRVKVSQAAAD  GI 1353498
 1  MKGETPVNSTMSIG-----QARKMVEQLKIEASLCRIKVSKAAAD   GI 995917
 1  MKGETPVNSTMSIG-----QARKMVEQLKIEASLCRIKVSKAAAD   GI 163084

41  LMTYCDAHACEDPLITPVPTSENPFREKKFFCALL             112808
29  LMTYCDAHACEDPLITPVPTSENPFREK                    GI 1353498
41  LLAYCEAHVREDPLIPVPASENPFREKKFFCTIL              GI 995917
41  LMTYCDAHACEDPLITPVPTSENPFREKKFFCALL             GI 163084
```

HUMAN GTP BINDING PROTEIN GAMMA-3

FIELD OF THE INVENTION

The present invention relates to nucleic acid and amino acid sequences of a novel disease associated membrane protein (HGPG) and to the use of these sequences in the diagnosis, study, prevention, and treatment of disease.

BACKGROUND

The heterotrimeric G proteins, a family of GTPases, are present in all cells. They control a variety of functions (metabolic, humoral, neural and developmental) by transducing hormonal, neurotransmitter and sensory signals into an array of cellular responses. Triggered by cell surface receptors, each G protein regulates the activity of a specific effector. The effectors include adenylate cyclase, phospholipase C, and ion channel proteins which initiate appropriate biochemical responses. G proteins can exhibit strict subcellular localization and can be included in endocytic vesicles.

Each G protein is composed of alpha ($\alpha$), beta ($\beta$) and gamma ($\gamma$) subunits associated as a complex in the inactive, GDP-bound form. Activation of a transmembrane receptor by a hormone results in activation of the GTPase and replacement of GDP by GTP. When activated, the heterotrimer, the a subunit, or the $\beta$-$\gamma$ subunit may have specific activity. Generally, the a subunit of a G protein disassociates from the $\beta$ and $\gamma$ complex, interacts with receptors and carries the message to the effector.

There are at least 20 genes for G$\alpha$ subunits which encode four major classes of proteins with at least 56–95% amino acid identity. The stimulatory, Gs class, is sensitive to pertussis toxin which uncouples the receptor:G protein interaction. This uncoupling blocks signal transduction to those receptors that decrease the cAMP which regulates ion channels and activates phospholipases. The inhibitory, Gi class, is also susceptible to modification by pertussis toxin which prevents Gi from lowering cAMP levels. Two novel classes refractory to pertussis toxin modification, are Gq which activates phospholipase C and $G_{12}$ which has sequence homology with the Drosophila gene *concertina* and may contribute to the regulation of embryonic development. The G$\alpha$ subunits range in molecular weight from 39–52 kDa and include some splice variants. Multiple genes also encode at least four $\beta$ and six $\gamma$ subunits which range in molecular weight from 35–36 kDa and 6–10 kDa, respectively (Watson S and S Arkinstall (1994) *The G protein Linked Receptor Facts Book*, Academic Press, San Diego Calif.).

The $\beta$-$\gamma$ dimer promotes the association of the GDP-bound a subunit with ligand-bound receptor. The dimer both orients and stabilizes the association so that signal transduction does not occur in the absence of agonist. Neer E. J. (1995; Cell 80:249–257) reported that $\beta$-$\gamma$ dimers interact with adenylyl cyclase, phospholipase C, calmodulin, $\beta$ adrenergic receptor kinase, phospholipase A2, phosducin, phosphoinositide 3-kinase, transducin, etc. In addition, the dimer may regulate potassium channels, mediate mitogen-activated protein kinase pathways and activate or increase phosphoinositide hydrolysis. In yeast, the dimer mediates a G protein-dependent mating response. Although the five $\beta$ subunit isotypes share 53–90% amino acid identity and are expressed ubiquitously, Clapman D. E. and E. J. Neer (1993; Nature 365:403–6) reported that $\beta$-4 is more abundant in brain and lung than in other tissues.

The known $\gamma$ subunits from bovine, rat and mouse tissues are most divergent in their N-terminal sequence. The $\gamma$ subunits generally display at least one cysteine residue in approximately the middle of their amino acid sequence which is important for dimer formation, ie, the cysteine in the $\gamma$ subunit cross links with a cysteine in the $\beta$ subunit. Many of the sequences show a C-terminal consensus sequence CAAX (where A represents aliphatic residues and X is unspecified) which resembles the ras oncogene terminal sequence and is a site for post-translational modification. The modification involves cleavage of the 3' terminal residues and subsequent carboxymethylation, farnesylation, geranylgeranylation or isoprenylation. Post-translational modification increases subunit diversity and hydrophobicity and is important for membrane association and functional activity. In contrast, the rat $\gamma$-5 sequence which terminates in CSFL is widely expressed and was highly expressed in kidney, heart, lung, and brain.

Although the different G proteins subunits could form some 600 different combinations, not all combinations are possible or functional. In the case of dimers, the $\beta$1-$\gamma$ 1 is only active in retina. Furthermore, the pattern of effector regulation may be highly specific. For example, whereas one type of adenylyl cyclase is activated by the Ga subunit and unaffected by the $\beta$-$\gamma$ subunit, a second type is activated by a subunit and inhibited by $\beta$-$\gamma$ subunit. In another example involving the pituitary-derived GH3 cell line, the somatostatin receptor and the muscarinic receptor both regulate calcium channels, but each uses an alternatively spliced form of the $a_{s/o}$ and different $\beta$-$\gamma$ subunits. A final example addresses specificity and efficiency; in reconstituted vesicles, the $\beta$-adrenergic receptor activates Gs as much as 3-fold better than Gi and the $\beta$-$\gamma$ subunits from either heterotrimer should activate the potassium channel, however, only adenylyl cyclase is activated.

Neer (supra) suggests that G protein regulation depends on a combination of factors including the kinetics of ATP hydrolysis, stoichiometry, covalent modification, accessory proteins and compartmentalization, and that the number of receptors exceeds the number of G proteins. The molecular and functional diversity of Gs-stimulated adenylyl cyclases was recently reviewed by Iyengar R (1993; FASEB Jour 7:768–75), and different tissues were shown to express a variety of adenylyl cyclases which were differentially regulated by the $\beta$-$\gamma$ dimers and other molecules.

Diseases Associated with Cell Signaling Molecules and Pathways

Mutations in the molecules and alterations in the expression pattern of the components of the cell signaling cascade may result in abnormal activation of leukocytes or lymphocytes or cellular proliferation which affects growth and development. Inappropriate activation of leukocytes or lymphocytes may result in the tissue damage and destruction seen in autoimmune diseases such as rheumatoid arthritis, biliary cirrhosis, hemolytic anemia, lupus erythematosus, and thyroiditis. For example, Aussel C et al. (1988; J Immunol 140–215) reported that T cell activation is a G protein regulated process. Work in Jurkat cells with pertussis toxin showed that G protein serves as a transducer for signals via the T cell receptor-CD3 complex. In addition, the fact that fluoride ions stimulate the release of diacylglycerol but not inositol phosphate 3 further suggests that G proteins control the activity of phospholipase C.

Abnormal proliferation of cells can cause endometriosis or tumors, adenomas or carcinomas. Cyclic AMP stimulation of brain, thyroid, adrenal, and gonadal tissue proliferation is regulated by G proteins. In fact, about 50 percent of growth hormone-producing pituitary adenomas contain a mutated $Ga_s$ allele, and similar mutations have been associated with thyroid carcinomas and the neoplastic lesions of McCune-Albright syndrome. A known mutation in the $Ga_{2i}$ gene is found in tumors derived from adrenal cortex and ovary. Persistent extracellular stimulation and expression of those receptors coupled to Gq and phospholipase C can also result in tumor formation (Isselbacher K. J. et al (1994) Harrison's Principles of Internal Medicine, McGraw-Hill, New York N.Y.). In addition, multiple endocrine hyperfunction may be due to defects in the G protein-cyclic AMP-protein kinase A-dependent pathway.

Phosphoinositide 3 kinase is a key signaling enzyme implicated in receptor stimulated mitogenesis, oxidative bursting in neutrophils, membrane ruffling and glucose uptake. Stephens L et al. (1994; Cell 77:83–93) report that phosphoinositide 3 kinase activation in myeloid derived cells is regulated by β-γ dimers as well as phosphotyrosine kinase. Furthermore, it appears that tissue specificity may be governed by concentration of β-γ dimer molecules and that activation is more rapid and transient than that regulated by phosphotyrosine kinase. Although it was not suggested, it appears that the ability to control expression of either β or γ subunits provides a means to regulate cell signaling and mitogenesis.

The discovery of new G subunit proteins, their functional combinations and their interactions with receptors can satisfy a need in the art by providing opportunities to intercede in abnormal cell processes. The activation of G proteins and the rate of GTP hydrolysis can be altered by controlling subunit production and association. Preventing dimer and heterotrimer formation can diminish cell signaling in GTP regulated pathways, reducing the activation of second messengers and controlling activation of leukocytes and lymphocytes and cell proliferation associated with tumor formation.

SUMMARY OF THE INVENTION

The present invention discloses a novel disease associated membrane protein, hereinafter referred to as HGPG, which shares features with four transmembrane spanning proteins involved in regulating cell proliferation. Accordingly, the invention features a substantially purified HGPG, as shown in the amino acid sequence of SEQ ID NO:1.

One aspect of the invention features isolated and substantially purified polynucleotides which encode HGPG. In a particular aspect, the polynucleotide is the nucleotide sequence of SEQ ID NO:2. In addition, the invention features polynucleotide sequences that hybridize under stringent conditions to SEQ ID NO:2.

The invention further relates to the nucleic acid sequence encoding HGPG, oligonucleotides, peptide nucleic acids, fragments, portions or antisense molecules thereof. The present invention also relates, in part, to the inclusion of the nucleic acid sequence encoding HGPG in an expression vector which can be used to transform host cells or organisms and produce the protein. The invention provides for using similar vectors to express antisense molecules to prevent proliferation of cancerous cells or anappropriate activation of the immune system.

The instant invention presents a method for producing HGPG or a fragment thereof. It contemplates the delivery of antagonists or inhibitors of HGPG, alone or in a pharmaceutically acceptable excipient, to cancerous or inflamed cells or tissues. It also encompasses antibodies which bind specifically to HGPG and can be used to examine prevalence of the protein in vivo.

BRIEF DESCRIPTION OF THE FIGURES

FIGS. 1A and 1B show the amino acid (SEQ ID NO:1) and nucleic acid sequences (SEQ ID NO:2) of the novel HGPG of the present invention. The alignment was produced using MacDNAsis software (Hitachi Software Engineering Co Ltd, San Bruno, Calif.).

FIG. 2 shows the amino acid sequence alignments among HGPG (SEQ ID NO:1) and mouse G protein γ 3 subunit (GI 1353498; Williams CJ et al. (1996) Mol Reprod Dev:in press), human G protein γ 4 subunit (GI 995917; Ray K et al. (1995) J Biol Chem 270:21765–71), and bovine G protein γ 3 subunit (GI 163084; Gautam N et al. (1990)Proc Natl Acad Sci 87:7973–77). Sequences were aligned using the multisequence alignment program of DNAStar™ software (DNAStar Inc, Madison, Wis.).

DESCRIPTION OF THE INVENTION

Definitions

Figure 3:
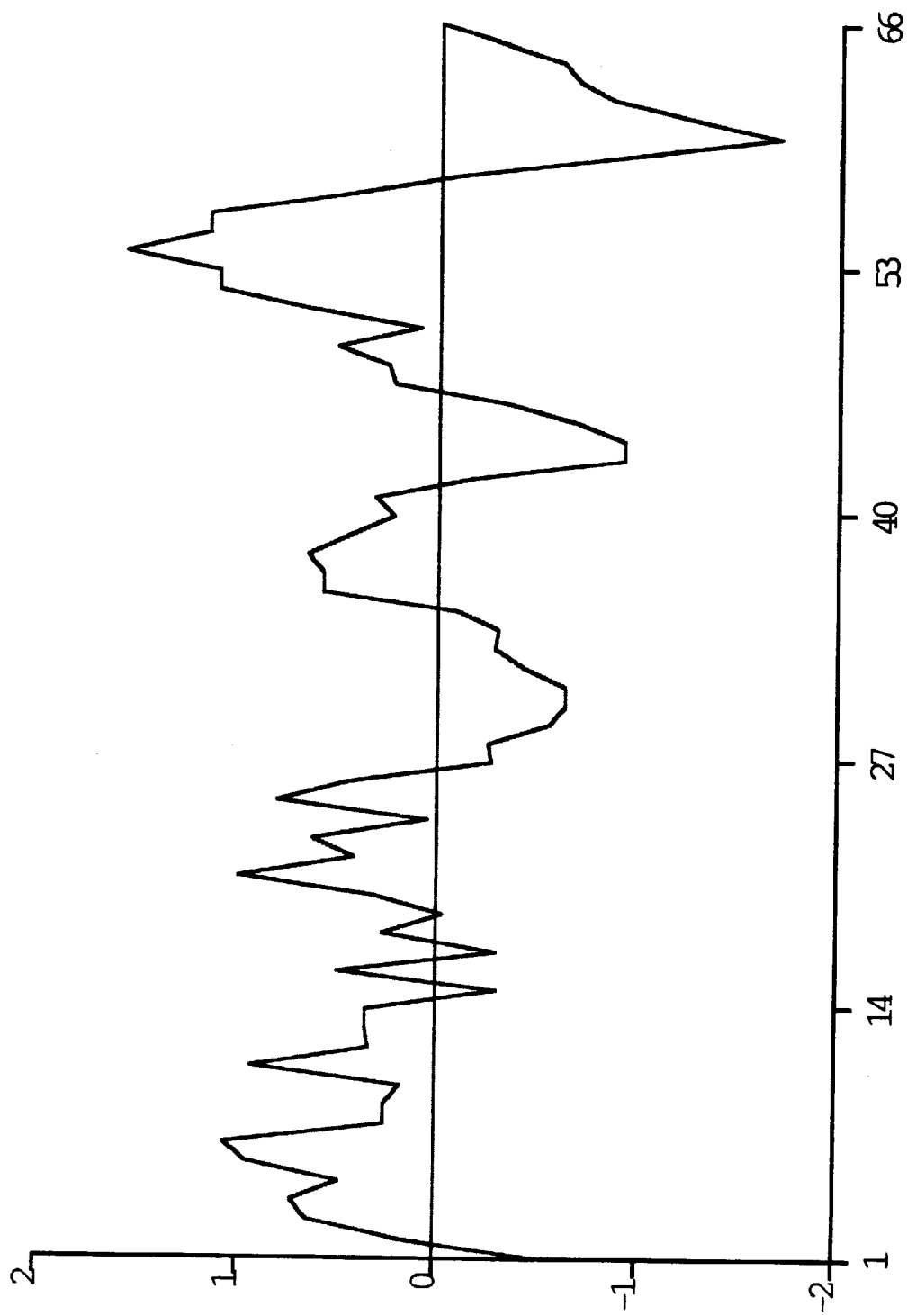
FIG. 3 shows the hydrophobicity plot (generated using MacDNAsis software) for HGPG, SEQ ID NO:1; the X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Consensus" as used herein may refer to a nucleic acid sequence 1) which has been resequenced to resolve uncalled bases, 2) which has been extended using XL-PCR (Perkin Elmer, Norwalk, Conn.) in the 5' or the 3' direction and resequenced, 3) which has been assembled from the overlapping sequences of more than one Incyte clone GCG Fragment Assembly System, (GCG, Madison, Wis.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P. E. et al (1993) Anticancer Drug Des 8:53–63).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring HGPG.

A "substitution" results from the replacement of one or more nucleotides or amino acids by different nucleotides or amino acids, respectively.

As used herein, HGPG refers to the amino acid sequence of substantially purified HGPG obtained from any species, particularly mammalian, including bovine, ovine, porcine, murine, equine, and preferably human, from any source whether natural, synthetic, semi-synthetic or recombinant.

A "variant" of HGPG is defined as an amino acid sequence which differs by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to HGPG having structural, regulatory or biochemical functions of a naturally occurring HGPG. Likewise, "immunologically active" defines the capability of the natural, recombinant or synthetic HGPG, or any oligopeptide thereof, to induce a specific immune response in appropriate animals or cells and to bind with specific antibodies.

The term "derivative" as used herein refers to the chemical modification of a nucleic acid encoding HGPG or the encoded HGPG. Illustrative of such modifications would be replacement of hydrogen by an alkyl, acyl, or amino group. A nucleic acid derivative would encode a polypeptide which retains essential biological characteristics of natural HGPG.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

The term "hybridization" as used herein shall include "any process by which a strand of nucleic acid joins with a complementary strand through base pairing" (Coombs J (1994) *Dictionary of Biotechnology*, Stockton Press, New York, N.Y.). Amplification is defined as the production of additional copies of a nucleic acid sequence and is generally carried out using polymerase chain reaction technologies well known in the art (Dieffenbach C. W. and G. S. Dveksler (1995) *PCR Primer, a Laboratory Manual*, Cold Spring Harbor Press, Plainview, N.Y.). "Stringency" typically occurs in a range from about Tm–5° C. (5° C. below the Tm of the probe) to about 20° C. to 25° C. below Tm. As will be understood by those of skill in the art, stringent hybridization can be used to identify or detect identical polynucleotide sequences or to identify or detect similar or related polynucleotide sequences.

Preferred Embodiments

The present invention relates to a novel human G protein γ 3 subunit (HGPG) which was identified among the cDNAs of the pituitary library (PITUNOT01) and to the use of the nucleic acid and amino acid sequences in the study, diagnosis, prevention and treatment of disease.

The nucleic acid sequence (SEQ ID NO:2) encoding HGPG was first identified within Incyte Clone No. 112808 using BLAST (Basic Local Alignment Search Tool; Altschul S. F. (1993) J Mol Evol 36:290–300; Altschul S. F. et al (1990) J Mol Biol 215:403–10) and showed homology to the bovine G protein γ-3 subunit (GI 163084).

The consensus sequence of SEQ ID NO:2 was extended and assembled using Incyte Clones 90963 (HYPONOB01), 112808 (PITUNOT01), 489878, 491492 (HNT2AGT01), 658952, 660806 (BRAINOT03), 926890 (BRAINOT04), 1229795 (BRAITUT01), 1384744 (BRAITUT08), and 1480453 (CORPNOT02). Homology to mouse, human and bovine γ-3 subunits is shown in FIG. 2. Significant conserved amino acid residues include $C_{30}$, $C_{45}$, and $C_{50}$ and the 3' terminal consensus sequence, CALL, also seen in the bovine protein.

The HGPG Coding Sequences

The extended and assembled nucleic acid and deduced amino acid sequences of HGPG are shown in FIGS. 1A and 1B. In accordance with the invention, any nucleic acid sequence which encodes HGPG can be used to generate recombinant molecules which express HGPG. In a specific embodiment described herein, a partial sequence encoding HGPG was first isolated as Incyte Clone 112808 from a pituitary cDNA library (PITUNOT01).

It will be appreciated by those skilled in the art that as a result of the degeneracy of the genetic code, a multitude of HGPG-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring HGPG, and all such variations are to be considered as being specifically disclosed.

Although nucleotide sequences which encode HGPG and its variants are preferably capable of hybridizing to the nucleotide sequence of the naturally occurring sequence under appropriately selected conditions of stringency, it may be advantageous to produce nucleotide sequences encoding HGPG or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HGPG and its derivatives without altering the encoded amino acid sequences include the production of RNA transcripts having more desirable properties, such as a greater half-life, than transcripts produced from the naturally occurring sequence.

A DNA sequence, or portions thereof, encoding HGPG or its derivative may be produced entirely by synthetic chemistry. After synthesis, the gene may be inserted into any of the many available DNA vectors and cell systems using reagents that are generally available. Moreover, synthetic chemistry may be used to introduce mutations into a sequence encoding HGPG or any portion thereof.

Also included within the scope of the present invention are polynucleotide sequences that are capable of hybridizing to the nucleotide sequence of SEQ ID NO:2 under various conditions. Hybridization conditions are based on the melting temperature (Tm) of the nucleic acid binding complex or probe, as taught in Berger and Kimmel (1987, *Guide to Molecular Cloning Technigues, Methods in Enzymology*, Vol 152, Academic Press, San Diego, Calif.) incorporated herein by reference, and on the salt concentrations under which the steps of the process are carried out.

Altered nucleic acid sequences encoding HGPG which may be used in accordance with the invention include deletions, insertions or substitutions of different nucleotides resulting in a polynucleotide that encodes the same or a functionally equivalent HGPG. The protein may also show deletions, insertions or substitutions of amino acid residues which produce a silent change and result in a functionally equivalent HGPG. Deliberate amino acid substitutions may be made on the basis of similarity in polarity, charge, solubility, hydrophobicity, hydrophilicity, and/or the amphipathic nature of the residues as long as the biological activity of HGPG is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles encoding HGPG. As used herein, an "allele" or "allelic sequence" is an alternative form of the nucleic acid sequence encoding HGPG. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing may be used which are well known in the art and employ such enzymes as the Klenow fragment of DNA polymerase I, Sequenase® (US Biochemical Corp, Cleveland, Ohio)), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding HGPG may be extended utilizing partial nucleotide sequence and various methods known in the art to detect upstream sequences such as promoters and regulatory elements. For example, Gobinda et al (1993; PCR Methods Applic 2:318–22) use "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequence is walking PCR (Parker J. D. et al (1991) Nucleic Acids Res 19:3055–60), which involves targeted gene walking. Alternatively, PCR, nested primers, PromoterFinder™ (Clontech, Palo Alto, Calif.) and PromoterFinder libraries can be used to walk in genomic DNA. This process avoids the need to screen libraries and is useful in finding intron/exon junctions.

Preferred libraries for screening for full length cDNAs are those which have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton, Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M. C. et al (1993) Anal Chem 65:2851-8).

Expression of the Nucleotide Sequence

In accordance with the present invention, polynucleotide sequences which encode HGPG, fragments of the polypeptide, fusion proteins or functional equivalents thereof may be used in recombinant DNA molecules that direct the expression of HGPG in appropriate host cells. Due to the inherent degeneracy of the genetic code, other DNA sequences which encode substantially the same or a functionally equivalent amino acid sequence, may be used to clone and express HGPG. As will be understood by those of skill in the art, it may be advantageous to produce HGPG-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HGPG expression or to produce recombinant RNA transcripts having desirable properties, such as a longer half-life, than transcripts produced from naturally occurring sequence.

The nucleotide sequences of the present invention can be engineered in order to alter HGPG-encoding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant HGPG-encoding sequence may be ligated to a heterologous sequence to encode a fusion protein. For example, for screening of peptide libraries for inhibitors of HGPG activity, it may be useful to encode a chimeric HGPG protein that is recognized by a commercially available antibody. A fusion protein may also be engineered to contain a cleavage site located between HGPG and the heterologous protein sequence, so that the HGPG may be cleaved and substantially purified away from the heterologous moiety.

In an alternate embodiment of the invention, the sequence encoding HGPG may be synthesized, whole or in part, using chemical methods well known in the art (see Caruthers M. H. et al (1980) Nuc Acids Res Symp Ser 215–23, Horn T et al (1980) Nuc Acids Res Symp Ser 225–32, etc). Alternatively, the protein itself may be produced using chemical methods to synthesize an amino acid sequence for HGPG, whole or in part. For example, peptide synthesis can be performed using various solid-phase techniques (Roberge J. Y. et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, W. H. Freeman and Co, New York, N.Y.). The composition of the synthetic peptides may be confirmed by amino acid analysis or sequencing (eg, the Edman degradation procedure; Creighton, supra). Additionally the amino acid sequence of HGPG, or any part thereof, may be altered during direct synthesis and/or combined using chemical methods with sequences from other proteins, or any part thereof, to produce a variant polypeptide.

Expression Systems

In order to express a biologically active HGPG, the nucleotide sequence encoding HGPG or its functional equivalent, is inserted into an appropriate expression vector, ie, a vector which contains the necessary elements for the transcription and translation of the inserted coding sequence.

Methods which are well known to those skilled in the art can be used to construct expression vectors containing a sequence encoding HGPG and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview, N.Y. and Ausubel F. M. et al (1989) *Current Protocols in Molecular Biology*, John Wiley & Sons, New York, N.Y.

A variety of expression vector/host systems may be utilized to contain and express a sequence encoding HGPG. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSportl (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of the sequence encoding HGPG, vectors based on SV40 or EBV may be used with an appropriate selectable marker.

In bacterial systems, a number of expression vectors may be selected depending upon the use intended for HGPG. For example, when large quantities of HGPG are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the sequence encoding HGPG may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding HGPG may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R. M. (1991) Results Probl Cell Differ 17:85–105) may be used. These constructs can be introduced into plant cells by direct DNA transformation or pathogen-mediated transfection. For reviews of such techniques, see Hobbs S or Murry L. E. in McGraw Hill *Yearbook of Science and Technology* (1992) McGraw Hill New York, N.Y., pp 191–196 or Weissbach and Weissbach (1988) *Methods for Plant Molecular Biology*, Academic Press, New York N.Y., pp 421–463.

An alternative expression system which may be used to express HGPG is an insect system. In one such system, *Autographa californica* nuclear polyhedrosis virus (AcNPV) is used as a vector to express foreign genes in *Spodoptera frugiperda* cells or in Trichoplusia larvae. The sequence encoding HGPG may be cloned into a nonessential region of the virus, such as the polyhedrin gene, and placed under control of the polyhedrin promoter. Successful insertion of the sequence encoding HGPG will render the polyhedrin gene inactive and produce recombinant virus lacking coat protein coat. The recombinant viruses are then used to infect *S. frugiperda* cells or Trichoplusia larvae in which HGPG is expressed (Smith et al (1983) J Virol 46:584; Engelhard E. K. et al (1994) Proc Nat Acad Sci 91:3224–7).

In mammalian host cells, a number of viral-based expression systems may be utilized. In cases where an adenovirus is used as an expression vector, a sequence encoding HGPG may be ligated into an adenovirus transcription/ translation complex consisting of the late promoter and tripartite leader sequence. Insertion in a nonessential E1 or E3 region of the viral genome will result in a viable virus capable of expressing in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a sequence encoding HGPG. These signals include the ATG initiation codon and adjacent sequences. In cases where the sequence encoding HGPG, its initiation codon and upstream sequences are inserted into the most appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express HGPG may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S. C. and R. C. Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes, C. A. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the sequence encoding HGPG is inserted within a marker gene sequence, recombinant cells containing the sequence encoding HGPG can be identified by the absence of marker gene function. Alternatively, a marker gene can be placed in tandem with the sequence encoding HGPG under the control of a single promoter. Expression of the marker gene in response to induction or selection usually indicates expression of the tandem sequence as well.

Alternatively, host cells which contain the sequence encoding HGPG and expressing HGPG may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding HGPG can be detected by DNA—DNA or DNA—RNA hybridization or amplification using probes, portions or fragments of the sequence encoding HGPG. Nucleic acid amplification based assays involve the use of oligonucleotides or oligomers based on the nucleic acid sequence to detect transformants containing DNA or RNA encoding HGPG. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer. A variety of protocols for detecting and measuring the expression of HGPG, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HGPG is preferred, but a competitive binding assay may be employed. These and other assays are described, among other places, in Hampton R et al (1990, *Serological Methods, a Laboratory Manual*, APS Press, St Paul, Minn.) and Maddox D. E. et al (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the HGPG-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of HGPG

Host cells transformed with a nucleotide sequence encoding HGPG may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing sequence encoding HGPG can be designed with signal sequences which direct secretion of HGPG through a prokaryotic or eukaryotic cell membrane. Other recombinant constructions may join the sequence encoding HGPG to nucleotide sequence encoding a polypeptide domain which will facilitate purification of soluble proteins (Kroll D. J. et al (1993) DNA Cell Biol 12:441–53; cf discussion of vectors infra containing fusion proteins).

HGPG may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequences such as Factor XA or enterokinase (Invitrogen, San Diego, Calif.) between the purification domain and HGPG is useful to facilitate purification. One such expression vector provides for expression of a fusion protein comprising the sequence encoding HGPG and nucleic acid sequence encoding 6 histidine residues followed by thioredoxin and an enterokinase cleavage site. The histidine residues facilitate purification while the enterokinase cleavage site provides a means for purifying HGPG from the fusion protein.

In addition to recombinant production, fragments of HGPG may be produced by direct peptide synthesis using solid-phase techniques (cf Stewart et al (1969) *Solid-Phase Peptide Synthesis*, W. H. Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Various fragments of HGPG may be chemically synthesized separately and combined using chemical methods to produce the full length molecule.

Uses of HGPG

The rationale for diagnostic and therapeutic uses of sequences encoding HGPG is based on the nucleotide and amino acid sequences, their homology to the mouse G protein γ-3 subunit, their tissue distribution primarily in brain, but also in bone marrow, breast, kidney and placenta and the known associations and functions of heterotrimeric and dimeric G proteins.

The nucleic acid sequence presented in FIGS. 1A and 1B, its complement, fragments or oligomers, and anti-HGPG antibodies may be used as diagnostic compositions in assays of cells, tissues or their extracts. Purified GPG or the nucleotide encoding it can be used as the positive controls in their respective protein or nucleic acid based assays for conditions or diseases characterized by the excess expression of HGPG. Antisense molecules, antagonists or inhibitors capable of specifically binding HGPG can be used as pharmaceutical compositions for conditions or diseases characterized by expression of HGPG. Such conditions include cell proliferation associated with tumor formation.

The regulation of γ-3 subunit expression or of dimer formation and activity provides an opportunity for early intervention in conditions based on cell proliferation. In this case, the main use would be in specifically inhibiting the growth of brain or breast tumors. For such inhibition, a vector containing and capable of expressing antisense sequences of SEQ ID NO:2, peptide nucleic acids (PNA), or inhibitors of HGPG can be introduced during biopsy or after surgery. Delivery of these therapeutic molecules, further described below under Pharmaceutical Compositions, is necessarily tissue/tumor specific and depends on the diagnosis, size and status of the neoplasm or tumor.

The expression of the β-3 subunit was also noted in bone marrow, kidney placenta and in the corpus callosum of a subject with Alzheimer's disease. In these tissue the expression of the γ-3 subunit would likely be associated with leukocyte or lymphocyte activity. Supplying an inhibitor which would prevent dimer formation and activation would prevent unwarranted destruction in these tissues. Similarly delivery of an antisense molecule would prevent expression.

HGPG Antibodies

HGPG-specific antibodies are useful for the diagnosis and treatment of conditions and diseases associated with expression of HGPG. Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

It is not necessary that the portion of HGPG used for antibody induction have biological activity; however, the protein fragment, or oligopeptide must be antigenic. Peptides used to induce specific antibodies may have an amino acid sequence consisting of at least five amino acids, and preferably at least 10 amino acids. Preferably, they should mimic a portion of the amino acid sequence of the natural protein and may contain the entire amino acid sequence of a small, naturally occurring molecule. Short stretches of HGPG amino acids may be fused with those of another protein such as keyhole limpet hemocyanin and antibody produced against the chimeric molecule. Procedures well known in the art can be used for the production of antibodies to HGPG.

For the production of antibodies, various hosts including goats, rabbits, rats, mice, etc may be immunized by injection with HGPG or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HGPG may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York, N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HGPG-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for HGPG may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W. D. et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HGPG and its specific antibody and the measurement of complex formation. A two-site, monoclonal-based immunoassay utilizing monoclonal antibodies reactive to two noninterfering epitopes on a specific HGPG protein is preferred, but a competitive binding assay may also be employed. These assays are described in Maddox D. E. et al (1983, J Exp Med 158:1211).

Diagnostic Assays Using HGPG Specific Antibodies

Particular HGPG antibodies are useful for the diagnosis of conditions or diseases characterized by expression of HGPG or in assays to monitor patients being treated with HGPG, its fragments, agonists or inhibitors. Diagnostic assays for HGPG include methods utilizing the antibody and a label to detect HGPG in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HGPG, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HGPG is preferred, but a competitive binding assay may be employed. These assays are described, among other places, in Maddox, D. E. et al (1983, J Exp Med 158:1211).

In order to provide a basis for diagnosis, normal or standard values for HGPG expression must be established. This is accomplished by combining body fluids or cell extracts taken from normal subjects, either animal or human, with antibody to HGPG under conditions suitable for complex formation which are well known in the art. The amount of standard complex formation may be quantified by comparing various artificial membranes containing known quantities of HGPG with both control and disease samples from biopsied tissues. Then, standard values obtained from normal samples may be compared with values obtained from samples from subjects potentially affected by disease. Deviation between standard and subject values establishes the presence of disease state.

Drug Screening

HGPG, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HGPG and the agent being tested, may be measured.

Another technique for drug screening which may be used for high throughput screening of compounds having suitable binding affinity to the HGPG is described in detail in PCT/WO 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HGPG and washed. Bound HGPG is then detected by methods well known in the art. Substantially purified HGPG can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HGPG specifically compete with a test compound for binding HGPG. In this manner, the antibodies can be used to detect the presence of any peptide which shares one or more antigenic determinants with HGPG.

Uses of the Polynucleotide Encoding HGPG

A polynucleotide sequence encoding HGPG or any part thereof may be used for diagnostic and/or therapeutic purposes. For diagnostic purposes, the sequence encoding HGPG of this invention may be used to detect and quantitate gene expression in biopsied tissues in which HGPG may be expressed in response to oncogenes. The diagnostic assay is useful to distinguish between absence, presence, and excess expression of HGPG and to monitor regulation of HGPG levels during therapeutic intervention. Included in the scope of the invention are oligonucleotide sequences, antisense RNA and DNA molecules, and peptide nucleic acids.

Another aspect of the subject invention is to provide for hybridization or PCR probes which are capable of detecting polynucleotide sequences, including genomic sequences, encoding HGPG or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring HGPG, alleles or related sequences.

Probes may also be used for the detection of related sequences and should preferably contain at least 50% of the nucleotides from any of these sequences encoding HGPG. The hybridization probes of the subject invention may be derived from the nucleotide sequence of SEQ ID NO:2 or from genomic sequence including promoter, enhancer elements and introns of the naturally occurring sequence encoding HGPG. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs include the cloning of nucleic acid sequences encoding HGPG or HGPG derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding HGPG may be used for the diagnosis of conditions or diseases with which the expression of HGPG is associated. For example, polynucleotide sequences encoding HGPG may be used in hybridization or PCR assays of fluids or tissues from biopsies to detect HGPG expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The HGPG-encoding nucleotide sequences disclosed herein provide the basis for assays that detect activation or induction associated with inflammation or disease. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding HGPG in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for HGPG expression must be established. This is accomplished by combining body fluids or cell extracts taken from normal subjects, either animal or human, with HGPG, or a portion thereof, under conditions suitable for hybridization or amplification. Standard hybridization may be quantified by comparing the values obtained for normal subjects with a dilution series of HGPG run in the same experiment where a known amount of substantially purified HGPG is used. Standard values obtained from normal samples may be compared with values obtained from samples from patients affected by HGPG-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, may be used as described in U.S. Pat. Nos. 4,683,195 and 4,965,188 provides additional uses for oligonucleotides based upon the sequence encoding HGPG. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P. C. et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or calorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to EMAP-II and its expression profile, the polynucleotide encoding HGPG disclosed herein may be useful in the treatment of immune deficiency diseases.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense of the sequence encoding HGPG. See, for example, the techniques described in Sambrook et al (supra) and Ausubel et al (supra).

The polynucleotides comprising full length cDNA sequence and/or its regulatory elements enable researchers to use the sequence encoding HGPG as an investigative tool in sense (Youssoufian H and H. F. Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding HGPG can be turned off by transfecting a cell or tissue with expression vectors which express high levels of a desired HGPG fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of the sequence encoding HGPG, ie, the promoters, enhancers, and introns. Oligonucleotides derived from the transcription initiation site, eg, between –10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J. E. et al (In: Huber B. E. and B. I. Carr (1994) *Molecular and Immunologic Approaches*, Futura Publishing Co, Mt Kisco, N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding HGPG.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HGPG. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences encoding HGPG disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence encoding HGPG can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C. M. (1993; Blood Rev 7:127–34) and Trask B. J. (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York, N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a sequence encoding HGPG on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson T. J. et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HGPG, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that HGPG can be used to screen for therapeutic molecules which would ameliorate the adverse effects of inflammatory cells in autoimmune diseases.

The examples below are provided to illustrate the subject invention and are not included for the purpose of limiting the invention.

EXAMPLES

I DNA Library Construction

The pituitary library was constructed from a pooled sample of 21 whole, normal pituitary glands from human brains of Caucasian males and females with a range of ages from 16–70 years. The poly A+ RNA was obtained from Clontech (catalogue #6584-1 and #6584-2; Clontech Laboratories Inc. Palo Alto, Calif.) and used by Stratagene (La Jolla, Calif.) to custom construct the cDNA library.

The cDNA synthesis was primed using both oligo d(T) and random hexamers, and the two cDNA preparations were treated separately. Synthetic adapter oligonucleotides were ligated onto cDNA ends enabling insertion into the Stratagene Uni-ZAP™ vector system. Finally, the two CDNA libraries were combined into a single library by mixing equal numbers of bacteriophage.

The pituitary cDNA library was screened with either DNA probes or antibody probes and the pBluescript® phagemid (Stratagene) can be rapidly excised in vivo. The phage particles were transfected into E. coli host strain XL1-Blue® (Stratagene). Alternative unidirectional vectors may include but are not limited to pcDNAI (Invitrogen, San Diego, Calif.) and pSHlox-1 (Novagen, Madison, Wis.).

II Isolation and Sequencing of CDNA Clones

The phagemid forms of the individual CDNA clones were obtained by the in vivo excision process in which the host bacterial strain was co-infected with both the library phage and an f1 helper phage. Polypeptides or enzymes produced by both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified and used to reinfect fresh host cells (SOLR, Stratagene) which were selected on medium containing ampicillin.

Phagemid DNA was subsequently purified using the QIAWELL-8 Plasmid Purification System (QIAGEN Inc, Chatsworth, Calif.) and prepared for DNA sequencing and other analytical manipulations.

The cDNA inserts from random isolates of the pituitary library were sequenced in part. Methods for DNA sequencing are well known in the art. Conventional enzymatic methods employ DNA polymerase Klenow fragment, SEQUENASE™ (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-polyacrylamide gels and detected by fluorescence (for fluorescent-labeled precursors). Recent improvements in mechanized reaction preparation, sequencing, and analysis such as those using the Applied Biosystems Catalyst 800, 377 and 373 DNA sequencers use fluorescent detection methods.

III Homology Searching of CDNA Clones and Their Deduced Proteins

Each cDNA was compared to sequences in GenBank using a search algorithm developed by Applied Biosystems and incorporated into the INHERIT-670 Sequence Analysis System. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S. F. (1993) J Mol Evol 36:290–300; Altschul, S. F. et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques using BLAST (Altschul S. F. 1993 and 1990, supra) are used to search for identical or related molecules in nucleotide databases such as GenBank or the LIFESEQ™ database (Incyte, Palo Alto, Calif.). This analysis is much faster than multiple, membrane-based hybridizations. In addition, the sensitivity of the computer search can be modified to determine whether any particular match is categorized as exact or homologous. The basis of the search is the product score which is defined as:

% sequence identity×% maximum BLAST score100 and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search shown in FIG. 2 are reported as a list of libraries in which the HGPG encoding sequence occurs. Abundance and percentage abundance of the HGPG encoding sequence are also reported. Abundance directly reflects the number of times a particular transcript is represented in a cDNA library, and percent abundance is abundance divided by the total number of sequences examined in the cDNA library.

V Extension of the Sequence Encoding HGPG

The nucleic acid sequence of SEQ ID NO:2 is used to design oligo-nucleotide primers for extending a partial nucleotide sequence to full length or for obtaining 5'sequence from genomic libraries. One primer is synthesized to initiate extension in the antisense direction (XLR) and the other is synthesized to extend sequence in the sense direction (XLF). Primers allow the extension of the known sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 40° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [γ-$^{32}$P] adenosine triphosphate (Amersham, Chicago, Ill.) and T4polynucleotide kinase (DuPont NEN®, Boston, Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

The sequence encoding HGPG, or any part thereof, is used to inhibit in vivo or in vitro expression of naturally occurring sequence. Although use of antisense oligonucleotides, comprising about 20 base-pairs, is specifically described, essentially the same procedure is used with larger cDNA fragments. An oligonucleotide complementary to a portion of the coding sequence of HGPG as shown in SEQ ID NO:2 is used to inhibit expression of naturally occurring sequence. The complementary oligonucleotide is designed from the most unique 5' sequence and used either to inhibit transcription by preventing promoter binding to the upstream nontranslated sequence or translation of a transcript encoding HGPG by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIG. 1.

VIII Expression of HGPG

Expression of HGPG is accomplished by subcloning the cDNAs into appropriate vectors and transfecting the vectors into host cells. In this case, the cloning vector, pSport, previously used for the generation of the CDNA library is used to express HGPG in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HGPG. The signal sequence directs the secretion of HGPG into the bacterial growth media which can be used directly in the following assay for activity.

IX Assay for HGPG Activity

HGPG can readily be assayed in vitro by monitoring the mobilization of $Ca^{++}$ in neutrophil signal transduction pathways. Neutrophils are preloaded with purified HGPG and with a fluorescent dye such as FURA-2 or BCECF (Universal Imaging Corp) whose emission characteristics have been altered by $Ca^{++}$ binding. Then, the cells are exposed to allogeneic stimulation and $Ca^{++}$ flux is observed and quantified using a fluorescent activated cell sorter. Measurements of $CA^{++}$ flux are compared between cells in their normal state and those preloaded with HGPG. Increased mobilization attributable to increased HGPG availability results in increased emission.

X Production of HGPG Specific Antibodies

Figure 4:
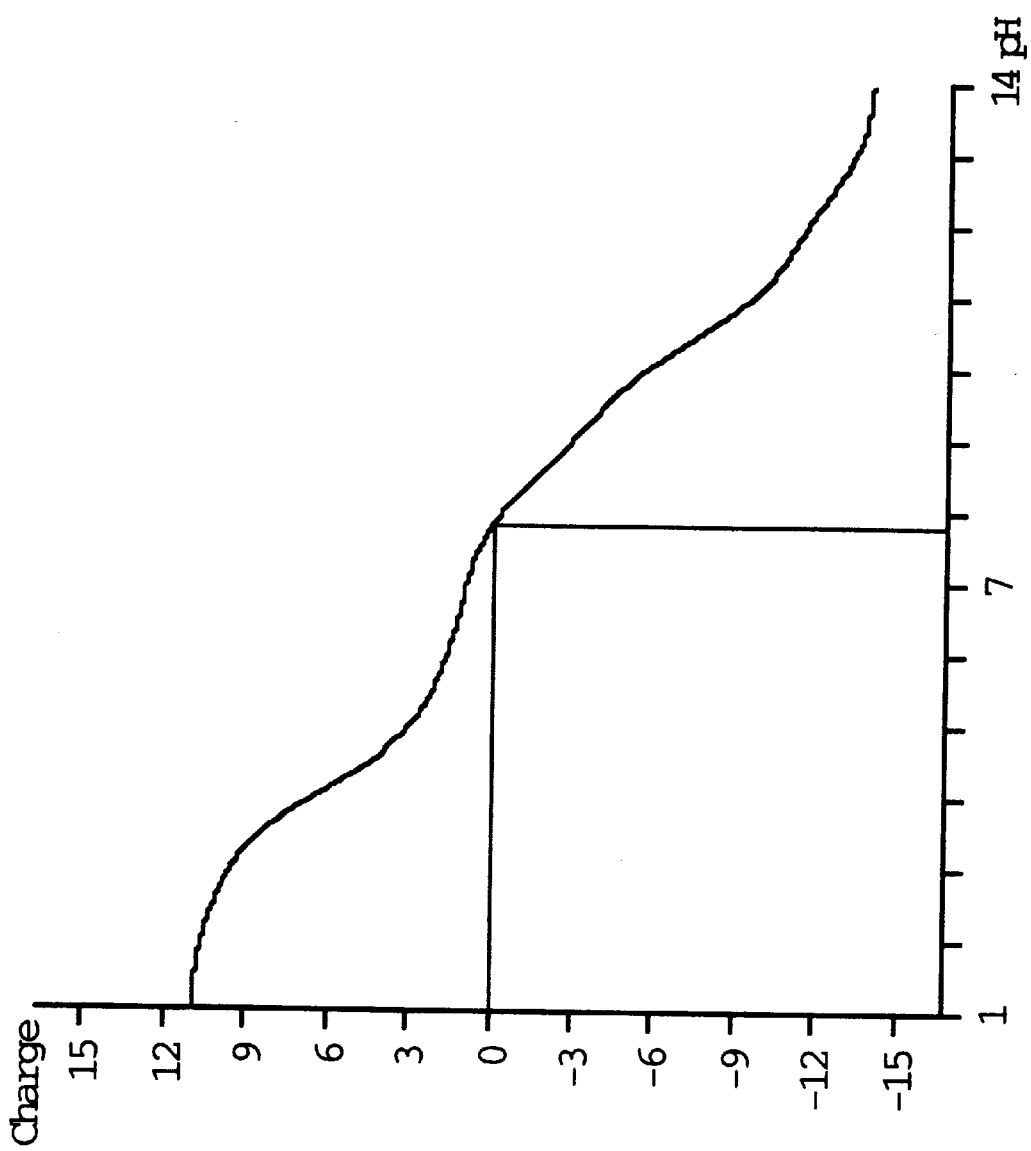
FIG. 4 shows the isoelectric plot (generated using MacDNAsis software) for HGPG, SEQ ID NO:1.

HGPG is substantially purified using PAGE electrophoresis (Sambrook, supra) is used to immunize rabbits and to produce antibodies using standard protocols. The amino acid sequence translated from HGPG is analyzed using DNAStar software (DNAStar Inc) to determine regions of high immunogenicity and a corresponding oligopeptide is synthesized and used to raise antibodies by means known to those of skill in the art. Analysis to select appropriate epitopes, such as those near the C-terminus or in hydrophilic regions (shown in FIGS. 4) is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F. M. et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HGPG Using Specific Antibodies

Naturally occurring or recombinant HGPG is substantially purified by immunoaffinity chromatography using antibodies specific for HGPG. An immunoaffinity column is constructed by covalently coupling HGPG antibody to an activated chromatographic resin such as CnBr-activated Sepharose (Pharmacia Biotech). After the coupling, the resin is blocked and washed according to the manufacturer's instructions.

Membrane fractions from cells expressing HGPG are prepared by methods well known in the art. Alternatively, a recombinant HGPG fragment containing an appropriate signal sequence may be secreted in useful quantity into the medium in which transfected cells are grown.

The HGPG-containing preparation is passed over the immunoaffinity column, and the column is washed under conditions that allow the preferential absorbance of HGPG (eg, high ionic strength buffers in the presence of detergent). The column is eluted under conditions that disrupt antibody/HGPG binding (eg, a buffer of pH 2–3 or a high concentration of a chaotrope such as urea or thiocyanate ion), and HGPG is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated polynucleotide sequence consisting of the nucleic acid sequence of SEQ ID NO:2.

2. An isolated polynucleotide sequence which is fully complementary to the isolated polynucleotide sequence of claim 1.

3. A recombinant expression vector containing the polynucleotide sequence of claim 1.

4. A recombinant host cell containing the expression vector of claim 3.

5. A method for producing the polypeptide of SEQ ID NO:1, the method comprising the steps of:

a) culturing the host cell of claim 4 under conditions suitable for the expression of the polypeptide; and b) recovering the polypeptide from the host cell culture.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 75 amino acids
       (B) TYPE: amino acid
       (C) STRANDEDNESS: single
       (D) TOPOLOGY: linear (ii) MOLECULE TYPE: peptide (vii) IMMEDIATE SOURCE:
       (A) LIBRARY: PITUNOT01
       (B) CLONE: 112808

(xi) SEQUENCE DESCRIPTION: SEQ ID NO:1:

Met Lys Gly Glu Thr Pro Val Asn Ser Thr Met Ser Ile Gly Gln Ala
1               5                   10                  15

Arg Lys Met Val Glu Gln Leu Lys Ile Glu Ala Ser Leu Cys Arg Ile
                20                  25                  30

Lys Val Ser Lys Ala Ala Ala Asp Leu Met Thr Tyr Cys Asp Ala His
                35                  40                  45

Ala Cys Glu Asp Pro Leu Ile Thr Pro Val Pro Thr Ser Glu Asn Pro
    50                  55                  60

Phe Arg Glu Lys Lys Phe Phe Cys Ala Leu Leu
65                  70                  75

(2) INFORMATION FOR SEQ ID NO:2:

(i) SEQUENCE CHARACTERISTICS:
       (A) LENGTH: 527 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
       (A) LIBRARY: PITUNOT01
       (B) CLONE: 112808

(xi) SEQUENCE DESCRIPTION: SEQ ID NO:2:

CCTTCAGGTA CCAGCCATCC AGACAGTGCT TGAGCTGCAG AAACTGAGAC CAGACCTCTG     60

GCCTGGCCCT CCCCAGGGGC CTCCTTTCCT ATAGTCACTG CTTCTGCATC AGATACTTTC    120

```
AGCTGCAACT CCCTACTGGG TGGGGCACCC ATTTCAGGCA GAAGGTTTTG GTACCCTCCA    180

CTGACCCTAC ACCCAGGGCT GCTACTGCCG CTTGTGGCTT CAGGATGAAA GGTGAGACCC    240

CGGTGAACAG CACTATGAGT ATTGGGCAAG CACGCAAGAT GGTGGAACAG CTTAAGATTG    300

AAGCCAGCTT GTGTCGGATA AAGGTGTCCA AGGCAGCAGC AGACCTGATG ACTTACTGTG    360

ATGCCCACGC CTGTGAGGAT CCCCTCATCA CCCCTGTGCC CACTTCGGAG AACCCCTTCC    420

GGGAGAAGAA GTTCTTCTGT GCTCTYCTCT GAGCTCCCCT GTCCCTTCTC ACAACTSCTC    480

CCTTTTCCCT CTCCTGGGCC CTTCCTTAGG TCAGTAATTG TTGTGAG                 527
```

(2) INFORMATION FOR SEQ ID NO:3:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1353498

(xi) SEQUENCE DESCRIPTION: SEQ ID NO:3:

```
Ile Gly Gln Ala Arg Lys Met Val Glu Gln Leu Lys Ile Glu Ala Ser
 1               5                  10                  15

Leu Cys Arg Ile Lys Val Ser Lys Ala Ala Ala Asp Leu Met Thr Tyr
                20                  25                  30

Cys Asp Ala His Ala Cys Glu Asp Pro Leu Ile Thr Pro Val Pro Thr
                35                  40                  45

Ser Glu Asn Pro Phe Arg Glu Lys
                50                  55
```

(2) INFORMATION FOR SEQ ID NO:4:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 995917

(xi) SEQUENCE DESCRIPTION: SEQ ID NO:4:

```
Met Lys Glu Gly Met Ser Asn Asn Ser Thr Thr Ser Ile Ser Gln Ala
 1               5                  10                  15

Arg Lys Ala Val Glu Gln Leu Lys Met Glu Ala Cys Met Asp Arg Val
                20                  25                  30

Lys Val Ser Gln Ala Ala Ala Asp Leu Leu Ala Tyr Cys Glu Ala His
                35                  40                  45

Val Arg Glu Asp Pro Leu Ile Ile Pro Val Pro Ala Ser Glu Asn Pro
    50                  55                  60

Phe Arg Glu Lys Lys Phe Phe Cys Thr Ile Leu
65                  70                  75
```

(2) INFORMATION FOR SEQ ID NO:5:

(i) SEQUENCE CHARACTERISTICS:

```
        (A) LENGTH: 75 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 163084

(xi) SEQUENCE DESCRIPTION: SEQ ID NO:5:

Met Lys Gly Glu Thr Pro Val Asn Ser Thr Met Ser Ile Gly Gln Ala
1               5                  10                  15

Arg Lys Met Val Glu Gln Leu Lys Ile Glu Ala Ser Leu Cys Arg Ile
            20                  25                  30

Lys Val Ser Lys Ala Ala Ala Asp Leu Met Thr Tyr Cys Asp Ala His
            35                  40                  45

Ala Cys Glu Asp Pro Leu Ile Thr Pro Val Pro Thr Ser Glu Asn Pro
    50                  55                  60

Phe Arg Glu Lys Lys Phe Phe Cys Ala Leu Leu
65                  70                  75
```